(12) United States Patent
Kim et al.

(10) Patent No.: US 10,772,586 B2
(45) Date of Patent: Sep. 15, 2020

(54) BACKSCATTERED RAY SHIELDING MECHANISM AND PORTABLE X-RAY GENERATING DEVICE COMPRISING SAME

(71) Applicants: VATECH Co., Ltd., Gyeonggi-do (KR); VATECH EWOO Holdings Co., Ltd., Gyeonggi-do (KR)

(72) Inventors: Yeong Kyun Kim, Gyeonggi-do (KR); Tae Woo Kim, Gyeonggi-do (KR); Min Seok Yun, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 156 days.

(21) Appl. No.: 15/778,788

(22) PCT Filed: Nov. 24, 2016

(86) PCT No.: PCT/KR2016/013661
§ 371 (c)(1),
(2) Date: May 24, 2018

(87) PCT Pub. No.: WO2017/091022
PCT Pub. Date: Jun. 1, 2017

(65) Prior Publication Data
US 2018/0344267 A1 Dec. 6, 2018

(30) Foreign Application Priority Data

Nov. 24, 2015 (KR) .......................... 10-2015-0164929

(51) Int. Cl.
*A61B 6/10* (2006.01)
*A61B 6/14* (2006.01)
(Continued)

(52) U.S. Cl.
CPC ................ *A61B 6/107* (2013.01); *A61B 6/10* (2013.01); *A61B 6/14* (2013.01); *A61B 6/4405* (2013.01);
(Continued)

(58) Field of Classification Search
CPC .. A61B 6/06; A61B 6/10; A61B 6/107; A61B 6/14; A61B 6/145; A61B 6/4405;
(Continued)

(56) References Cited

U.S. PATENT DOCUMENTS 7,020,238 B1 * 3/2006 Kantonen ............ G01N 23/223
378/102
7,375,358 B1 5/2008 Martin et al.
(Continued)

FOREIGN PATENT DOCUMENTS

| KR | 10-2008-0094968 A | 10/2008 |
|---|---|---|
| KR | 10-1211617 B1 | 12/2012 |
| KR | 2016124535 A * | 10/2016 |

OTHER PUBLICATIONS

Korean Intellectual Property Office, International Search Report of International Application No. PCT/KR2016/013661, dated Feb. 20, 2017.
(Continued)

*Primary Examiner* — Marcus H Taningco
(74) *Attorney, Agent, or Firm* — IP Legal Services, LLC

(57) ABSTRACT

Disclosed are a backscattered ray shielding mechanism and a portable X-ray generating device comprising the same. The backscattered ray shielding mechanism according to the present invention is mounted on a portable X-ray generating hand-held device to emit X-rays and blocking backscattered X-rays during X-ray emission and includes a lead-free lightweight shielding member, which is detachably or foldably mounted as a convertible form on an X-ray emitting
(Continued)

unit of the portable X-ray generating device and partially supported by the X-ray emitting unit.

12 Claims, 10 Drawing Sheets

(51) Int. Cl.
*G21K 1/10* (2006.01)
*H05G 1/02* (2006.01)
*A61B 6/00* (2006.01)
*G21F 1/08* (2006.01)
*G21F 3/00* (2006.01)
*H05G 1/06* (2006.01)
*A61B 6/06* (2006.01)

(52) U.S. Cl.
CPC .................. *A61B 6/56* (2013.01); *G21F 1/08* (2013.01); *G21F 3/00* (2013.01); *G21K 1/10* (2013.01); *H05G 1/02* (2013.01); *A61B 6/06* (2013.01); *A61B 6/145* (2013.01); *A61B 6/584* (2013.01); *H05G 1/06* (2013.01)

(58) Field of Classification Search
CPC .. A61B 6/56; A61B 6/584; G21F 1/08; G21F 3/00; G21K 1/10; H05G 1/02; H05G 1/06
See application file for complete search history.

(56) References Cited

U.S. PATENT DOCUMENTS

| | | |
|---|---|---|
| 8,787,523 B2* | 7/2014 | Sackett ................ G01N 23/223 378/117 |
| 2004/0232360 A1 | 11/2004 | Martin et al. |
| 2005/0078797 A1 | 4/2005 | Danielsson et al. |
| 2006/0098779 A1 | 5/2006 | Turner |
| 2007/0230659 A1 | 10/2007 | Turner |
| 2007/0269010 A1 | 11/2007 | Turner |
| 2008/0116394 A1 | 5/2008 | Grodzins |
| 2009/0220045 A1 | 9/2009 | Grodzins |
| 2013/0136238 A1 | 5/2013 | Laws et al. |
| 2013/0136239 A1 | 5/2013 | Laws et al. |
| 2015/0164443 A1 | 6/2015 | Laws et al. |

OTHER PUBLICATIONS

Korean Intellectual Property Office, Written Opinion of International Application No. PCT/KR2016/013661, dated Feb. 20, 2017.

* cited by examiner

BACKSCATTERED RAY SHIELDING MECHANISM AND PORTABLE X-RAY GENERATING DEVICE COMPRISING SAME

CROSS REFERENCE TO RELATED APPLICATIONS

This application is a National Stage Patent Application of PCT International Patent Application No. PCT/KR2016/013661 (filed on Nov. 24, 2016) under 35 U.S.C. § 371, which claims priority to Korean Patent Application No. 10-2015-0164929 (filed on Nov. 24, 2015), the teachings of which are incorporated herein in their entireties by reference.

TECHNICAL FIELD

The present invention relates to a backscattered ray shielding mechanism and a portable X-ray generating device comprising the same. More specifically, the present invention relates to a backscattered ray shielding mechanism and a portable X-ray generating device comprising the same in which the backscattered ray shielding mechanism is mounted on a portable X-ray generating hand-held device in order to emit X-rays, and blocks backscattered X-rays during X-ray emission to protect the user from X-ray exposure.

BACKGROUND ART

X-ray imaging modality is radiography using permeability of X-rays, in which an X-ray image of an inner structure of a subject is obtained based on an amount of attenuation that is accumulated in the process of the X-rays passing through the subject. To achieve image, an X-ray imaging device includes: an X-ray generating device emitting X-rays toward a subject; an X-ray sensor disposed to face the X-ray generating device with the subject therebetween, and configured to receive the X-rays having passed through the subject; and an image processor configured to produce an X-ray image of a field of view (FOV) by using a detection result of the X-ray sensor. The X-ray generating device has continually been downsized and improved in usability whereby the user frequently uses the X-ray generating device in easy way for diagnosis in hospitals and non-destructive inspection in industrial fields.

For example, such a small-sized X-ray generating device is utilized in a dental intraoral X-ray imaging modality. A small type of X-ray generating device such as a portable type or a hand-held type X-ray generating device is mainly used when a patient is uncomfortable to move or during a dental implant surgery, which needs rapid X-ray imaging modality. In this case, a compact X-ray sensor or a film is inserted in the oral cavity of the subject, and the user irradiates the oral structure with X-rays from the outside of the oral cavity toward the X-ray sensor or the like inserted into the oral cavity.

FIG. 1 is a diagram showing a portable X-ray generating device in the related art. Referring to FIG. 1, a portable X-ray generating device 10 in the related art is provided with a body 11 generating X-ray, an X-ray emitting unit 12 emitting the X-rays generated from the body 11 to a predetermined direction, and a handle 13 for a user to grab and to press a button for irradiating an object with X-rays. That is, the portable X-ray generating device 10 in the related art is advantageous for intraoral X-ray imaging because the user can grab the device, which may be a gun-type or a camera type, for irradiating an object with X-rays in various directions.

Such an X-ray imaging is very convenient for an examinee. On the other hand, the user is repeatedly exposed to backscattered radiation. It is known that when a user such as a hand 20 of a user is exposed to a backscattered ray for a long time, diseases and complications may occur. In order to prevent being exposed to radiation, there is an example in which a shielding body for shielding the backscattered rays is employed in a portable X-ray generating device of the related art.

FIG. 2 is a diagram showing a portable X-ray generating device in the related art. In the diagram, a body 11 of the portable X-ray generating device in which a small size of an X-ray generator is stored, and a shielding body 2 assembled around an X-ray emitting unit 12. Here, the shielding body 2 in the related art is made of lead acrylic which is thick and heavy, so it is difficult to hold the device by hand and to image without shaking. In addition, commercialized products have a thickness of about 12 mm and weigh about 500 g.

DISCLOSURE

Technical Problem

Accordingly, the present invention has been made keeping in mind the above problems occurring in the related art, and an object of the present invention is to provide a backscattered ray shielding mechanism capable of protecting a user from being exposed to backscattered rays during X-ray imaging with a portable X-ray generating device and being lightened for easy use. In addition, another object of the present invention is to provide an X-ray generating device having a convertible backscattered ray shielding mechanism, which is provided in a convertible form by being unfolded in use such that it is easy to store and use and being made of a light material, thereby stabilizing X-ray imaging.

Technical Solution

In order to accomplish the above object, a backscattered ray shielding mechanism according to the present invention, which is mounted on a portable X-ray generating hand-held device to emit X-rays and blocks backscattered X-rays during X-ray emission, includes: a lead-free lightweight shielding member detachably or foldably mounted as a convertible form on an X-ray emitting unit of the portable X-ray generating device and partially supported by the X-ray emitting unit.

The lead-free lightweight shielding member may be fitted around the X-ray emitting unit and includes at least one support member partially connected thereto to support the lead-free lightweight shielding member.

The X-ray emitting unit may be cylindrical and the at least one support member may be a ring rotating around the X-ray emitting unit or moving along a longitudinal direction of the X-ray emitting unit.

The lead-free lightweight shielding member may include an X-ray shielding material, which is lead-free and has a specific gravity smaller than that of lead. Here, the X-ray shielding material may be selected from a group consisting of tungsten, barium, bismuth, and mixtures thereof.

A backscattered ray shielding mechanism according to another aspect of the present invention, which is mounted on a portable X-ray generating hand-held device to emit X-rays and blocks backscattered X-rays during X-ray emission, includes: a support member detachably mounted around an X-ray emitting unit of the portable X-ray generating device; and a lead-free lightweight shielding sheet that is lead-free, has a specific gravity smaller than that of lead, is partially supported by the X-ray emitting unit, and is unfolded in a predetermined surface area to block backscattered rays.

Here, the support member may include: at least one support ring being fitted around the X-ray emitting unit; and at least one guide rail being attached to the support ring along a longitudinal direction of the X-ray emitting unit, wherein the shielding sheet is partially supported by the guide rail and moves along the guide rail.

Alternatively, the support member may include: at least one support ring being fitted around the X-ray emitting unit; and at least one connection bar being attached to the support ring along a longitudinal direction of the X-ray emitting unit and having first and second connection bars disposed along the longitudinal direction, wherein the first and second connection bars slide along with each other to overlap some parts thereof or are hinged to be bent such that each length thereof is adjusted and the shielding sheet moves according to the adjusted length thereof.

The shielding sheet may be provided as a curtain shape and suspended from the support member. Here, the shielding sheet may be woven tungsten filaments.

In order to accomplish the above object, a portable X-ray generating device includes: a body being provided with an X-ray generator; an X-ray emission port being disposed in front of the body from which X-rays are emitted; and a convertible backscattered ray shielding mechanism being mounted around the X-ray emission port of the body in a foldable form, and blocking backscattered rays in use and being folded to be stored when unused.

The convertible backscattered ray shielding mechanism may include: a rotation ring rotating around the X-ray emission port; and multiple shielding blades being folded and unfolded with association with a rotation of the rotation ring.

Alternatively, the convertible backscattered ray shielding mechanism may include: a rotation ring rotating around the X-ray emission port; multiple shielding strips being in close contact with each other and flaring with association with a rotation of the rotation ring; and a flexible shield connecting between the multiple shielding strips, and being configured to be folded when the multiple shielding strips are in close contact with each other and to be unfolded when the multiple shielding strips flare.

Alternatively, the convertible backscattered ray shielding mechanism may include: a sliding ring moving back and forth in an X-ray emission direction on a circumference of the X-ray emission port; multiple shielding strips configured to move each other to be closed or apart each other in depending on a position of the sliding ring and whose one ends are connected to the sliding ring; and a flexible shield being configured to be folded when the multiple shielding strips are in close contact with each other and to be unfolded when the multiple shielding strips flare.

Meanwhile, portable X-ray generating device may further include: an electric motor being connected to a power supply unit of the body; a power transmission unit performing folding and unfolding operations of the convertible backscattered ray shielding mechanism by using power of the electric motor; and a controller controlling the operation of the power transmission unit according to an input of a user.

Advantageous Effects

The present invention has the following effects.

When X-rays emitted from a portable X-ray generating device, a backscattered ray shielding mechanism according to the present invention can protect a hand of a user, etc. from backscattered rays and can be lightened, thereby alleviating the burden of the weight of the portable X-ray generating device. In addition, the backscattered ray shielding mechanism according to the present invention has excellent compatibility since the backscattered ray shielding mechanism can be applied to X-ray emitting units having different diameters. In addition, the backscattered ray shielding mechanism according to the present invention can freely adjust a distance between the hand of the user and a shielding sheet, which effectively blocks the backscattered rays according to a size of the user hand.

Furthermore, a portable X-ray generating device having a convertible backscattered ray shielding mechanism according to the present invention is easy to store and handle because the backscattered ray shielding mechanism is mounted on the body in a convertible form whereby only unfolded in use. The backscattered ray shielding mechanism is made of a lightweight material to reduce camera shakes, thereby stabilizing X-ray imaging. The X-ray generating device having the convertible backscattered ray shielding mechanism according to the present invention not only reduces the backscattered ray exposure to a user but also stabilizes X-ray imaging for accuracy, thereby reducing unnecessary X-ray exposure by re-imaging for an examinee.

MODE FOR INVENTION

Figure 1:
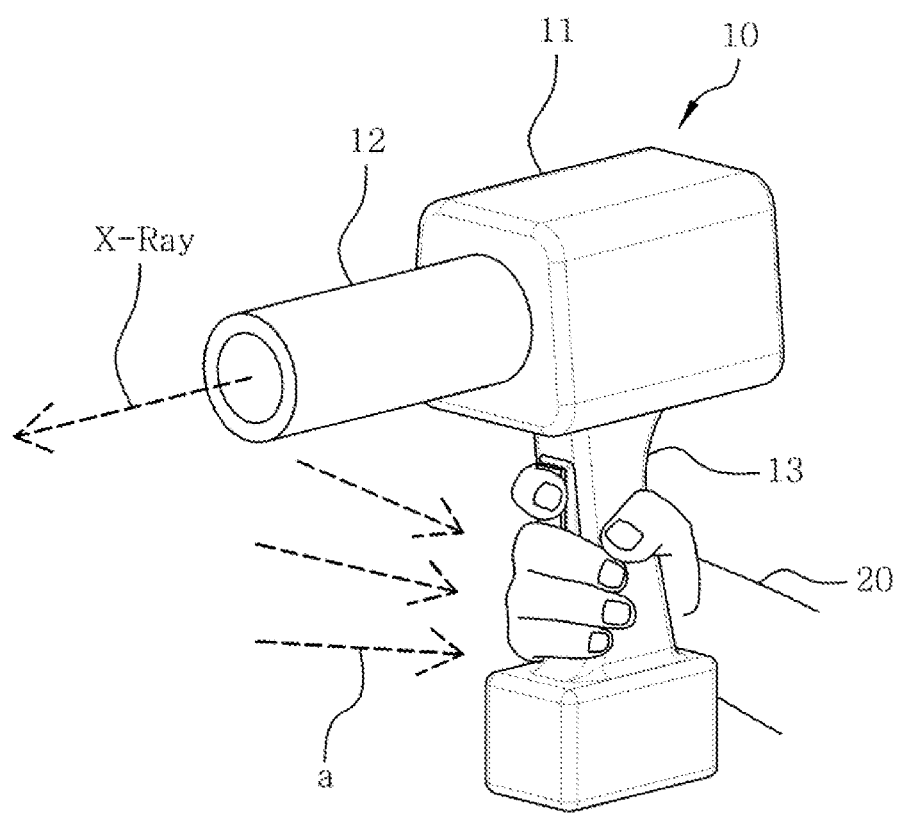
FIG. 1 is a diagram showing a portable X-ray generating device in the related art.

Hereinbelow, various embodiments of the present invention will be described in detail with reference to the accompanying drawings. A scope of the present invention may be clearly understood through the embodiments. The present invention is not limited to the embodiments described below and may be modified in various forms within the scope to which the present invention pertains. Meanwhile, like reference numerals used in several drawings denote a component having the same characteristics, and a description of the component having the same reference numeral as the component described with reference to any one drawing may be omitted from the description of another drawing.

Figure 3:
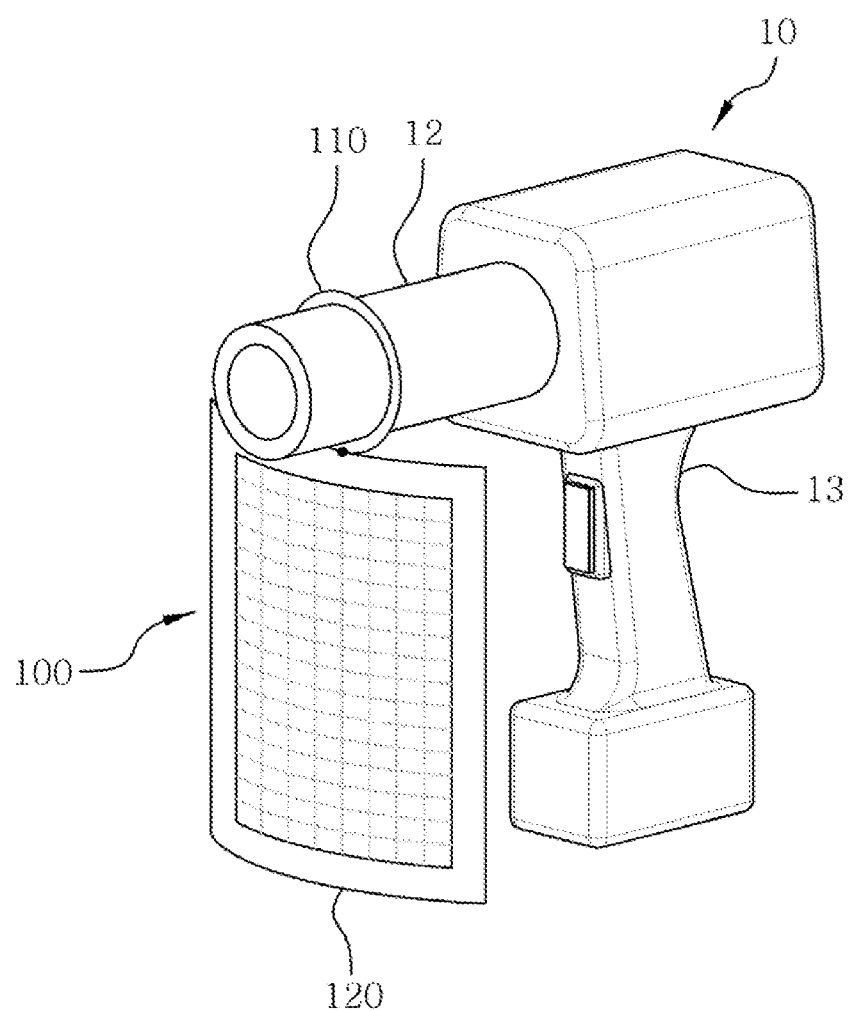
FIG. 3 is a diagram showing a backscattered ray shielding mechanism according to an embodiment of the present invention.

FIG. 3 is a diagram showing a backscattered ray shielding mechanism according to a first embodiment of the present invention.

Referring to FIG. 3, a backscattered ray shielding mechanism 100 according to the first embodiment of the present invention is provided with a support ring 110 as a support member and a shielding sheet 120 as a lead-free lightweight shielding member.

The support ring 110 is a supporting member detachably fitted around an X-ray emitting unit 12 of a portable X-ray generating device 10 by insertion, and fixing or suspending the shielding sheet 120 to be described below. The support ring 110 may be an elastic ring such as rubber to be fitted around the X-ray emitting unit 12 having a different diameter.

The support ring 110 is mounted to be capable of moving in a longitudinal direction of the X-ray emitting unit 12, and a distance between a handle 13 of the portable X-ray generating device 10 and the support ring 110 is changeable depending on a position of the support ring 110. This is so that the shielding sheet 120 can be suspended in a suitable position depending on a hand size of a user.

The shielding sheet 120 is a sheet having a predetermined surface area and blocking X-rays, and is attached to a lower end of the support ring 110 to be suspended from the X-ray emitting unit 12 downwardly. The shielding sheet 120 blocks backscattered rays, which are X-rays scattered to a hand of the user, to protect the hand of the user from being exposed to X-rays. It is preferable that the shielding sheet 120 is designed to be concave, i.e. opposite sides thereof are curved back toward the handle 13, thereby protecting the hand of the user from being exposed to the backscattered ray as much as possible.

The shielding sheet 120 may include an X-ray shielding material, which is lead-free and has a specific gravity smaller than that of lead. The shielding sheet 120 is not particularly limited as long as a sheet can block X-rays. For example, the shielding sheet 120 may be a lead-free (Pb-free) sheet or a tungsten sheet woven with tungsten filaments.

In short, the backscattered ray shielding mechanism 100 according to the first embodiment of the present invention is detachably mounted on the portable X-ray generating device 10 to protect a hand of a user from being exposed to the backscattered rays. In addition, being exposed to the backscattered rays can be effectively prevented by changing the position of the shielding sheet 120 depending on a hand size of the user.

Figure 4:
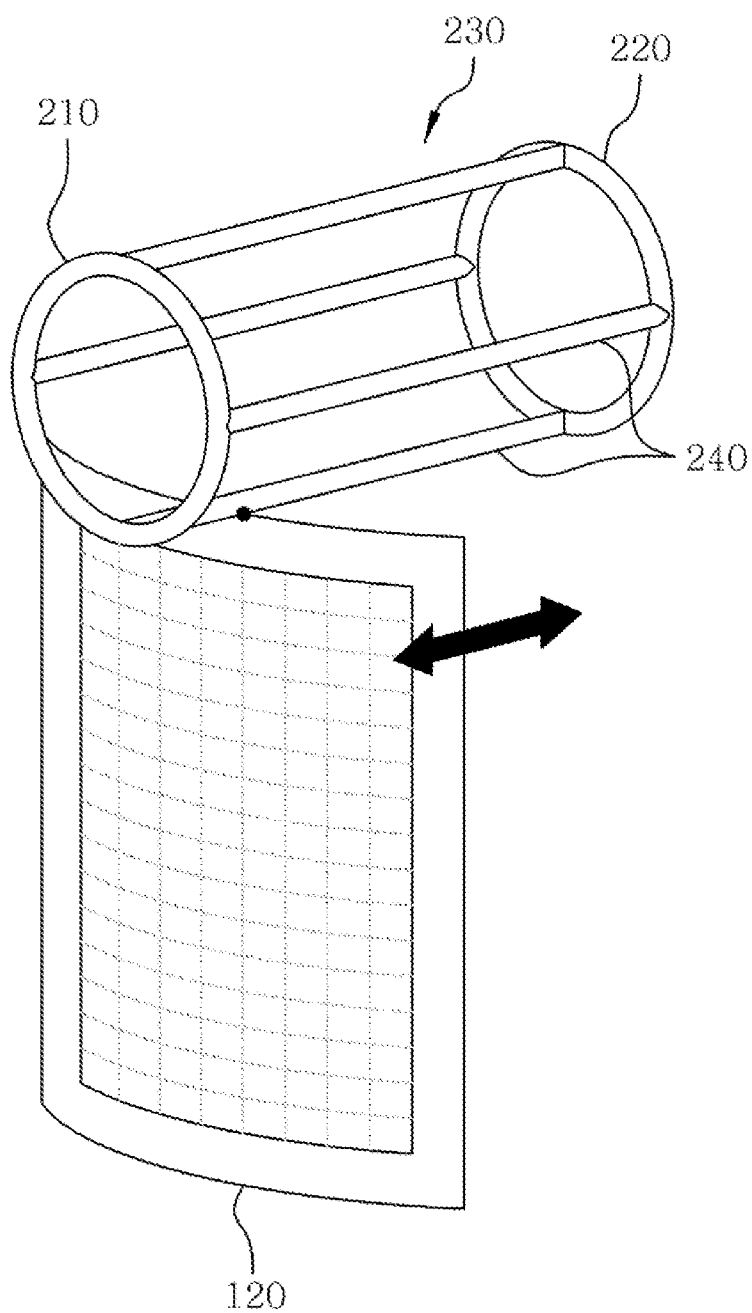
FIG. 4 is a diagram showing a backscattered ray shielding mechanism according to another embodiment of the present invention.

FIG. 4 is a diagram showing a backscattered ray shielding mechanism according to a second embodiment of the present invention.

Referring to FIG. 4, a backscattered ray shielding mechanism 200 according to the second embodiment of the present invention is provided with a first support ring 210 as a support member, a second support ring 220 being spaced apart from the first support ring 210 by a predetermined space, a plurality of guide rails 240 being spaced apart from each other in parallel and connecting the first support ring 210 and the second support ring 220 to each other, and a shielding sheet 120 being coupled to the guide rails 240 to move on the guide rails 240 back and forth.

Compared to the backscattered ray shielding mechanism 100 according to the first embodiment of the present invention, the backscattered ray shielding mechanism 200 according to the second embodiment of the present invention is provided with two support rings 210 and 220, which are fitted around the X-ray emitting unit 12 of the portable X-ray generating device 10, and the guide rails 240, which are added between the two support rings 210 and 220.

The support rings 210 and 220 are not moved along a longitudinal direction of the X-ray emitting unit 12 to change a position of the shielding sheet 120. In fact, the support rings 210 and 220 are fixedly disposed on a circumferential portion of the X-ray emitting unit 12 to be spaced apart from each other, and only the shielding sheet 120 moves on the guide rails 240 to change a position thereof.

Meanwhile, it is preferable that at least one of the support rings 210 and 220 is an elastic ring, and if necessary, elastic rings having different elastic forces may be used for convenient use. The shielding sheet 120 is substantially the same as the shielding sheet of the backscattered ray shielding mechanism 100 according to the first embodiment of the present invention.

Figure 5:
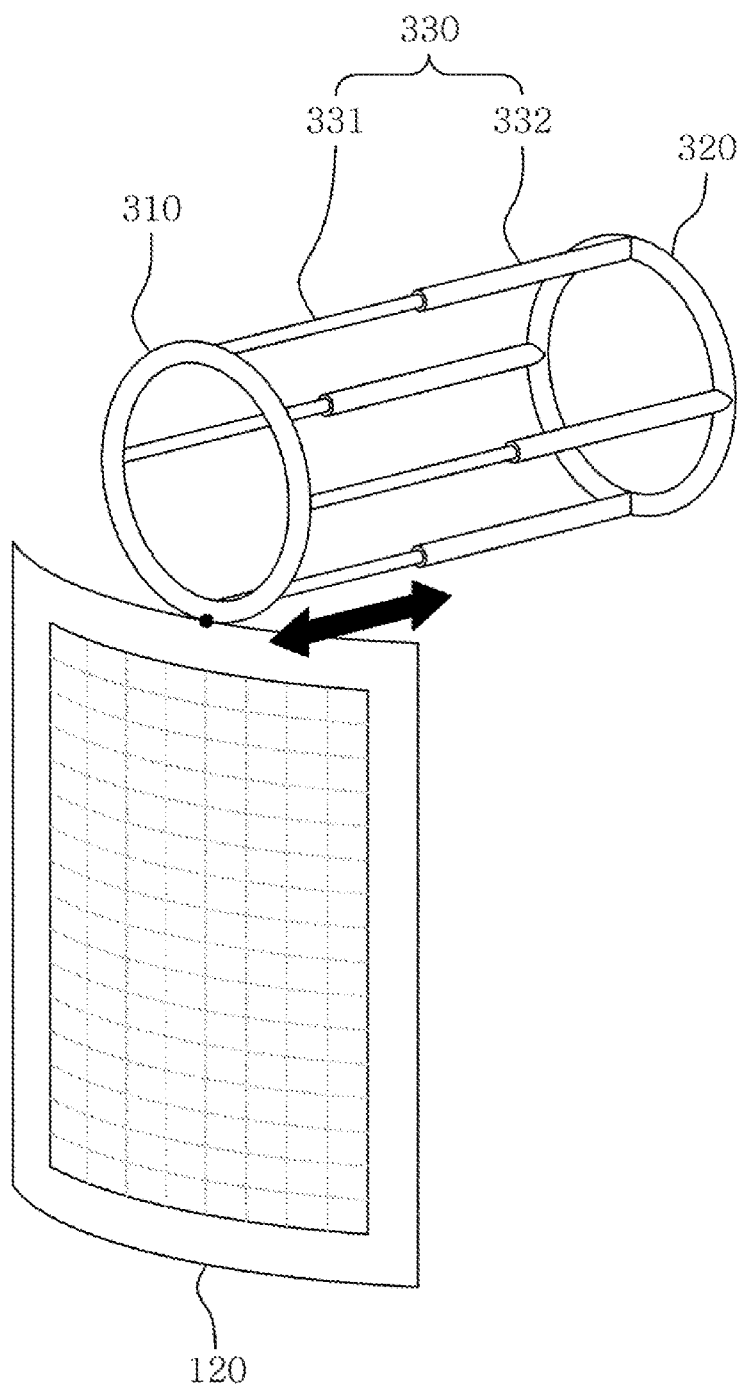
FIG. 5 is a diagram showing a backscattered ray shielding mechanism according to still another embodiment of the present invention.

FIG. 5 is a diagram showing a backscattered ray shielding mechanism according to a third embodiment of the present invention.

Referring to FIG. 5, a backscattered ray shielding mechanism 300 according to the third embodiment of the present invention is provided with a first support ring 310 as a support member, a second support ring 320 being spaced apart from the first support ring 310 by a predetermined space, a plurality of connection rods 330 being spaced apart from each other in parallel and connecting the first support ring 310 and the second support ring 320 to each other, and a shielding sheet 120 being coupled to the first support ring 310 to be suspended downwardly.

In addition, each of the connection rods 330 is provided as a first connection rod 331 and a second connection rod 332 such that the first connection rod 331 and the second connection rod 332 slide along with each other to overlap some parts thereof whereby an entire length thereof can be varied.

That is, compared to the backscattered ray shielding mechanism 200 according to the second embodiment of the present invention, the shielding sheet 120 of the backscattered ray shielding mechanism 300 according to the third embodiment of the present invention is not moved along the connection rod 330 to change the position thereof. In fact, the shielding sheet 120 of the backscattered ray shielding mechanism 300 according to the third embodiment of the present invention is fixed to the first support ring 310, and the position thereof is changed by back and forth movement of the first support ring 310.

Here, it is preferable that at least one of the support rings 310 and 320 is an elastic ring, and if necessary, elastic rings having different elastic forces may be used for convenient use. In addition, the shielding sheet 120 is substantially the same as the shielding sheet of the backscattered ray shielding mechanism 100 according to the first embodiment of the present invention.

Figure 6:
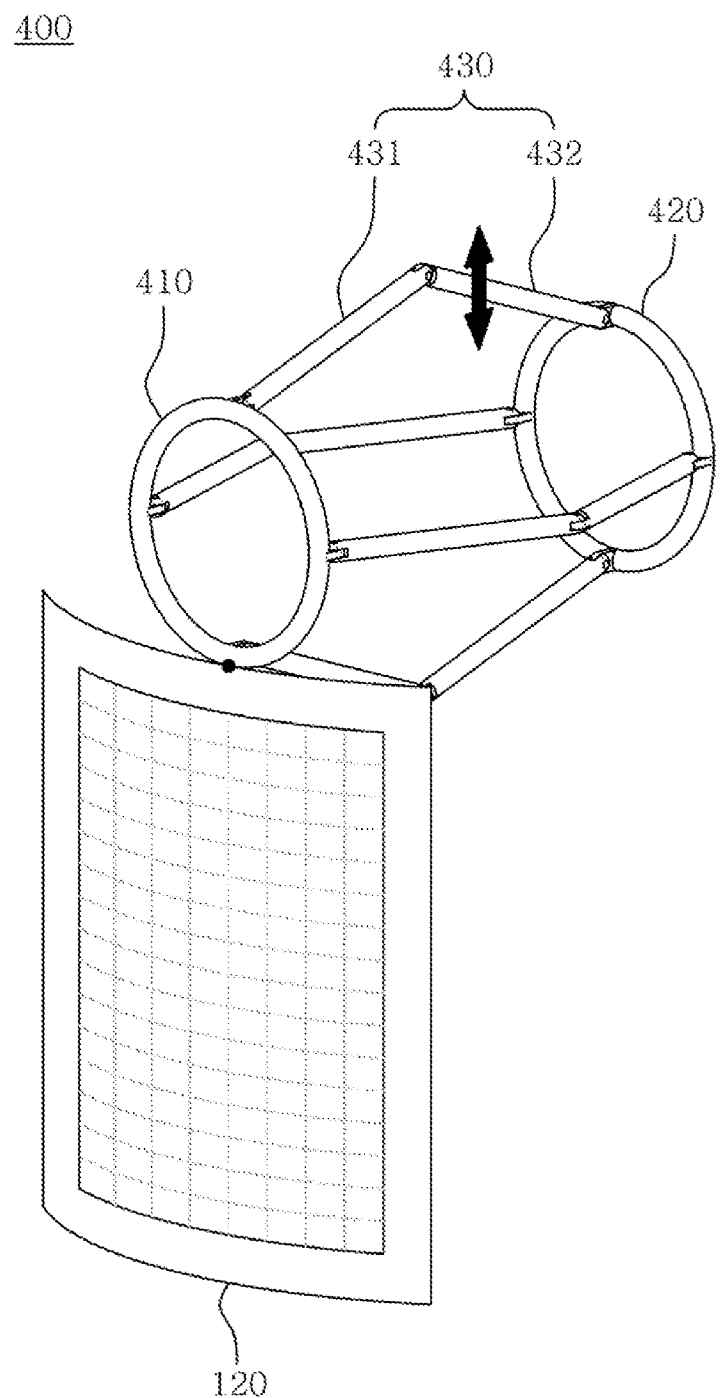
FIG. 6 is a diagram showing a backscattered ray shielding mechanism according to still another embodiment of the present invention.

FIG. 6 is a diagram showing a backscattered ray shielding mechanism according to a fourth embodiment of the present invention.

Referring to FIG. 6, a backscattered ray shielding mechanism 400 according to the fourth embodiment of the present invention is provided with a first support ring 410 as a support member, a second support ring 420 being spaced apart from the first support ring 410 by a predetermined space, a plurality of connection bars 430 being spaced apart from each other in parallel and connecting the first support ring 410 and the second support ring 420 to each other, and a shielding sheet 120 being coupled to the first support ring 310 to be suspended downwardly.

In addition, each of the connection bars 430 is provided such that first and second connection bars 431 and 432 are hinged to be bent. That is, as the connection bars 431 and 432 are bent, the first support ring 410 moves along a circumferential portion of the X-ray emitting unit 12, whereby a position of the shielding sheet 120 can be changed.

Here, it is preferable that at least one of the support rings 410 and 420 is an elastic ring, if necessary, elastic rings having different elastic forces may be used for convenient use. In addition, the shielding sheet 120 is substantially the same as the shielding sheet of the backscattered ray shielding mechanism 100 according to the first embodiment of the present invention.

Figure 7:
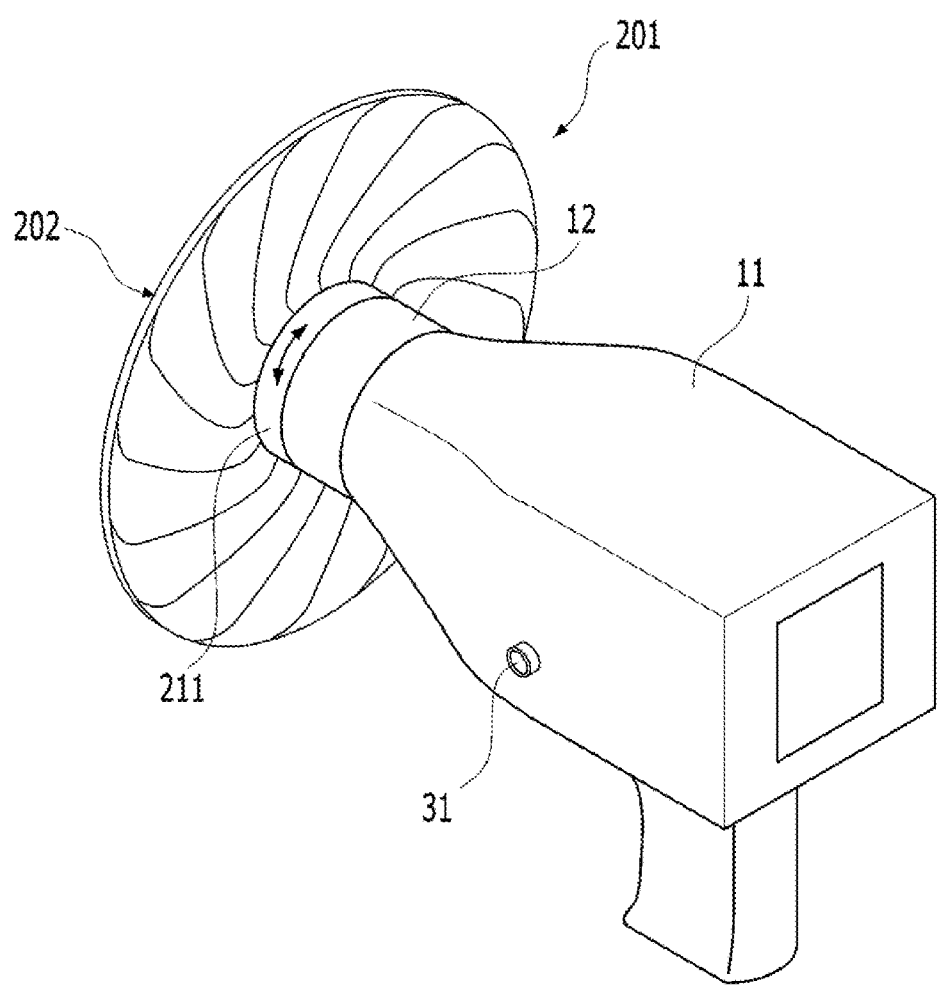
FIG. 7 is a diagram showing a convertible backscattered ray shielding mechanism of an X-ray generating device according to still another embodiment of the present invention is spread.

FIG. 7 is a diagram showing a convertible backscattered ray shielding mechanism of an X-ray generating device according to an embodiment of the present invention is spread.

The X-ray generating device according to the present invention may be, for example, a portable X-ray generating device provided with a handle on a body 11 in which a small size of an X-ray generator is stored such that a user can grab the handle. Portable X-ray generators are also called handheld types. Although an example of a portable X-ray generator is mainly described in the present invention, the present invention is not limited thereto and may be applied to X-ray generating devices used in connection with a device for supporting a movement of the X-ray generating devices, such as a standard arm.

A convertible backscattered ray shielding mechanism 201 is disposed near an X-ray emission port through which X-rays are emitted from the body 11, and the convertible backscattered ray shielding mechanism 201 is spread to shield the backscattered ray when used and folded and stored when not in use. A portion forming a periphery of the X-ray emission port is referred to as an X-ray emitting unit 12, and as an example, the convertible backscattered ray shielding mechanism 201 may be mounted to the X-ray emitting unit 12 and provided with a rotation ring 211 rotating around the X-ray emission port and a shielding member 202 being interlocked with a rotation of the rotation ring 211 and folded or unfolded according to a rotation direction of the rotation ring 211. Meanwhile, the diagram illustrates the embodiment of the rotary convertible backscattered ray shielding mechanism 201 that includes the rotation ring 211 and folds and unfolds the shielding member 202 by using the rotation of the rotation ring 211, but a specific embodiment of the present invention is not limited thereto. Various embodiments will be described later in detail and with specific examples.

The shielding member 202 functions to block backscattered rays that are scattered from an examinee or a subject and directed toward a user. The shielding member 202 may be configured to be folded or unfolded by a manual operation of the user and may be configured to be automatically folded or unfolded by an operation of a switch provided on the body 11. After the photographing is completed, the shielding member 202 is folded and stored in a small volume still in connection to the body 11 whereby it is unnecessary to separate the shielding member 202 from the body 11 and thus it is possible to eliminate the trouble of loss.

Meanwhile, the shielding member 202 may be configured as multiple shielding blades such that the multiple shielding blades may be configured to overlap each other and to be folded and unfolded. Alternatively, the shielding member 202 may be configured as a flexible shield. In order to prevent degradation of a shielding performance of the shielding member even after repeated use, the shielding member is manufactured in which bismuth, barium, or tungsten may be used independently or may be mixed with a resin or powders to achieve a shielding performance equal to that of lead having 0.25 mm in thickness or to achieve a shielding performance equal to that of lead having 0.5 mm in thickness. In addition, considering a direction of the backscattered rays, the shielding member 202 preferably has a diameter of 15 cm or more in the unfolded state, and a thickness thereof may be varied from about 0.2 mm to about 1.0 mm depending on the kind of material and required shielding performance.

Figure 2:
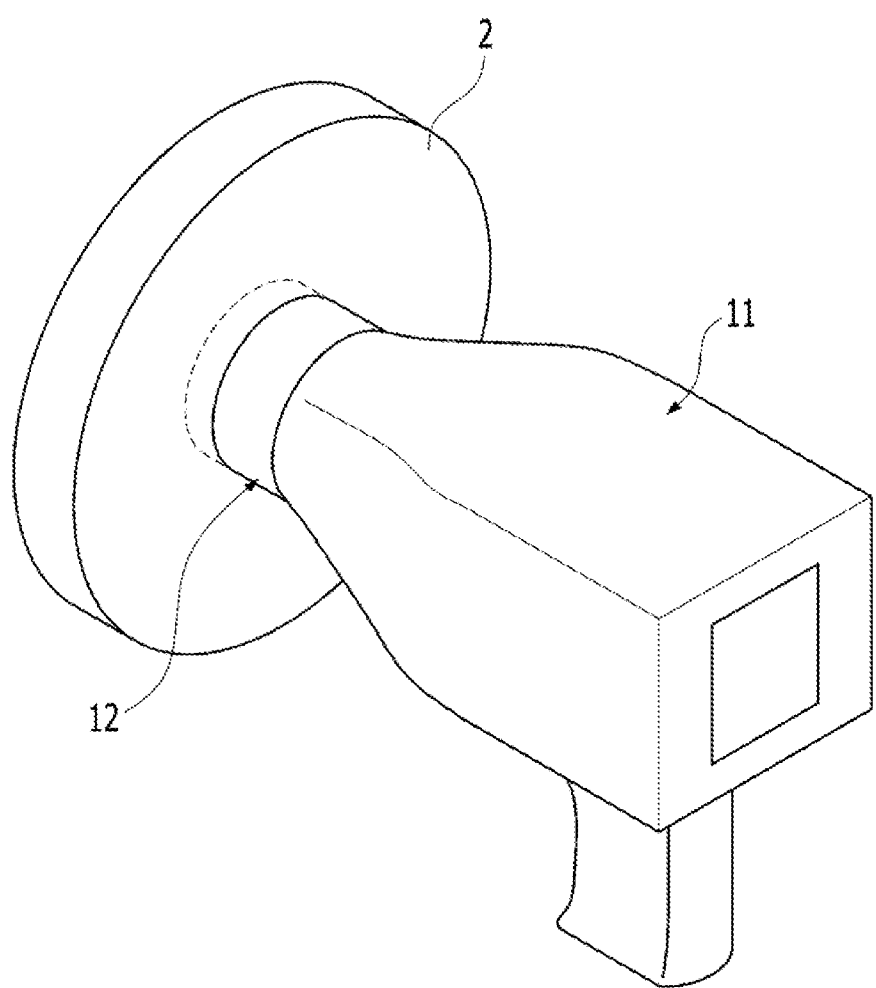
FIG. 2 is a diagram showing a portable X-ray generating device having a backscattered ray shielding body in the related art.

The shielding member 202 manufactured according to the above-described example may be implemented with a weight of 100 g or less excluding the mechanism structure. The weight is equivalent to about ⅕ to ¼ of a weight of the conventional shielding body shown in FIG. 2, which can greatly reduce camera shakes.

Figure 8:
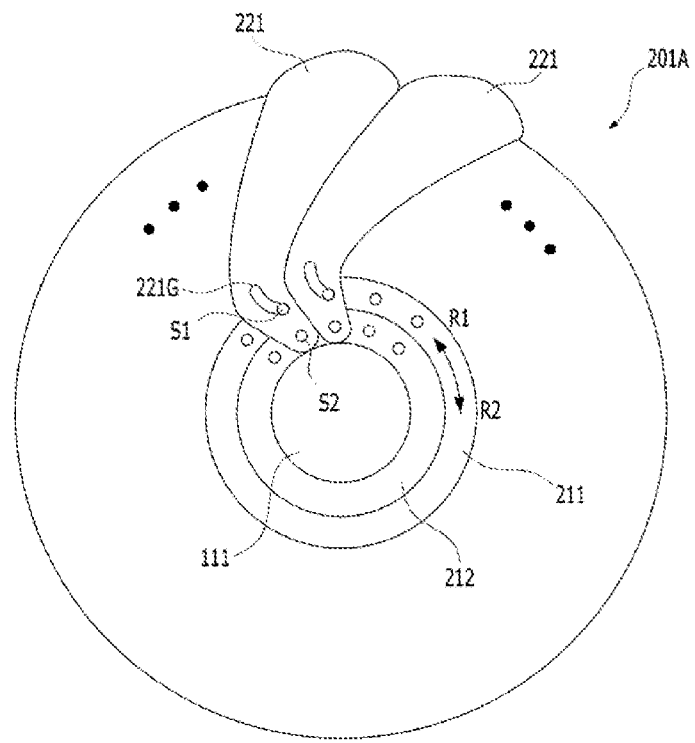
FIG. 8 is a diagram roughly showing a rotary convertible backscattered ray shielding mechanism according to still another embodiment of the present invention viewed from the front.

FIG. 8 is a diagram roughly showing a rotary convertible backscattered ray shielding mechanism according to an embodiment of the present invention viewed from the front.

A rotary convertible backscattered ray shielding mechanism 201A according to the embodiment of the present invention includes a first rotation ring 211, which is disposed near and rotates around an X-ray emission port 111. The first rotation ring 211 may be provided with a second rotation ring 212 at an inner side thereof. The first rotation ring 211 and the second rotation ring 212 rotate relatively, and any one of the first rotation ring 211 and the second rotation ring 212 may be fixed. Here, an example will be described in which the second rotary ring 212 is fixed with respect to the X-ray discharge port 111, and the first rotary ring 211 rotates in R1 and R2 directions along an outer periphery thereof.

The first rotation ring 211 and the second rotation ring 212 are connected to multiple shielding blades 221. As an example, the multiple shielding blades 221 are connected to a second stud S2 provided on the second rotation ring 212 and a first stud S1 provided on the first rotation ring 211. Here, the shielding blades 221 may be provided to rotate within a predetermined range by the first stud S1 about the second stud S2. Accordingly, the shielding blades 221 and the first stud S1 may be connected by a guide hole 221G formed in a predetermined shape. The guide hole 221G serves as a kind of cam for rotating the shielding blades 221 as relative positions of the first stud S1 and the second stud S2 are changed by the rotation of the first rotation ring 211. Thus, when the first rotation ring 211 rotates in the R1 direction with respect to the second rotation ring 212, the multiple shielding blades 221 are all unfolded such that the backscattered ray is blocked. On the contrary, when the first rotation ring 211 rotates in the R2 direction, the multiple shielding blades 221 are folded toward the outer periphery of the first rotation ring 211 and thus can be easily stored.

Figure 9:
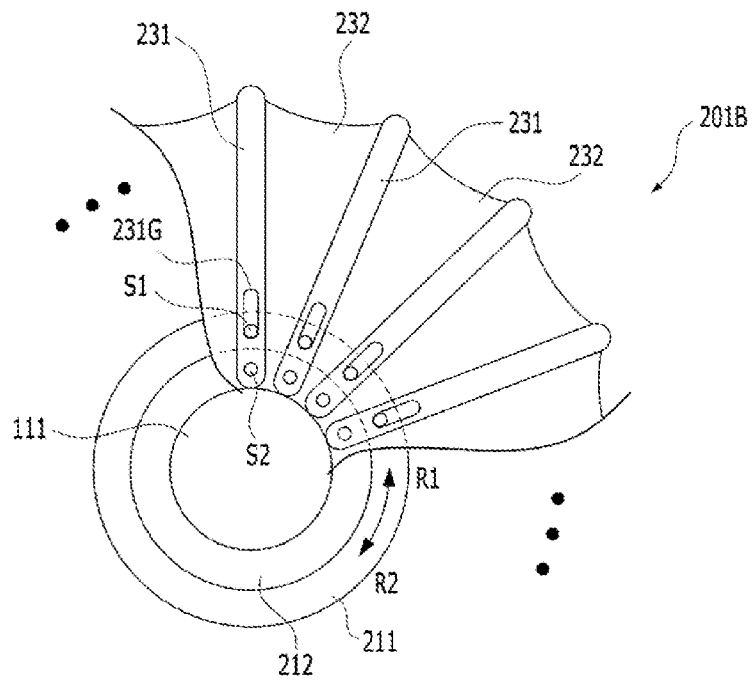
FIG. 9 is a diagram showing another example of the rotary convertible backscattered ray shielding mechanism according to still another embodiment of the present invention.

FIG. 9 is a diagram showing another example of the rotary convertible backscattered ray shielding mechanism according to the embodiment of the present invention.

According to the embodiment, a rotary convertible backscattered ray shielding mechanism 201B is provided with first and second rotary rings 211 and 212 that rotate relative to each other around an X-ray emission port 111, multiple shielding strips 231 that are in close contact with each other or flare in association with rotations of the first and second rotary rings 211 and 212, and a flexible shield 232 configured to be folded when the multiple shielding strips 231 are in close contact with each other and to be unfolded when the multiple shielding strips 231 flare.

The multiple shielding strips 231 may be made of a material having rigidity such as a metal and formed in a straight or curved shape. In the same manner as in the embodiment of FIG. 8, the multiple shielding strips 231 may be connected to a first stud S1 provided on the first rotation ring 211 and a second stud S2 provided on the second rotation ring 212. As an example, the multiple shielding strips 231 may be provided with a guide hole 231G connected to the first stud S1 such that the multiple shielding strips 231 rotate within a predetermined range about the second stud S2 by a relative position of the first stud S1 changed by a rotation of the first rotation ring 211.

The flexible shield 232 may be disposed between the multiple shielding strips 231, and configured to be folded when a gap between the multiple shielding strips 231 is narrowed and unfolded when the gap is widened. The multiple shielding strips 231 and the flexible shield 232 serve as the above-described shielding member, and a material of the flexible shield 232 has been described above with reference to FIG. 7 for the material of the shielding member.

An operation of the rotary convertible backscattered ray shielding mechanism 201B will be described. When the first rotation ring 211 rotates in an R1 direction with respect to the second rotation ring 212 and the first stud S1 and the second stud S2 are aligned on the radial line, the multiple shielding strips 231 are unfolded in the radial direction and the flexible shield 232 is also unfolded such that the backscattered ray is blocked. On the contrary, when the first rotation ring 211 rotates in an R2 direction, the first stud S1 and the second stud S2 become distant from each other and the multiple shielding strips 231 are folded toward the outer periphery of the first rotation ring 211 and thus can be easily stored.

Figure 10:
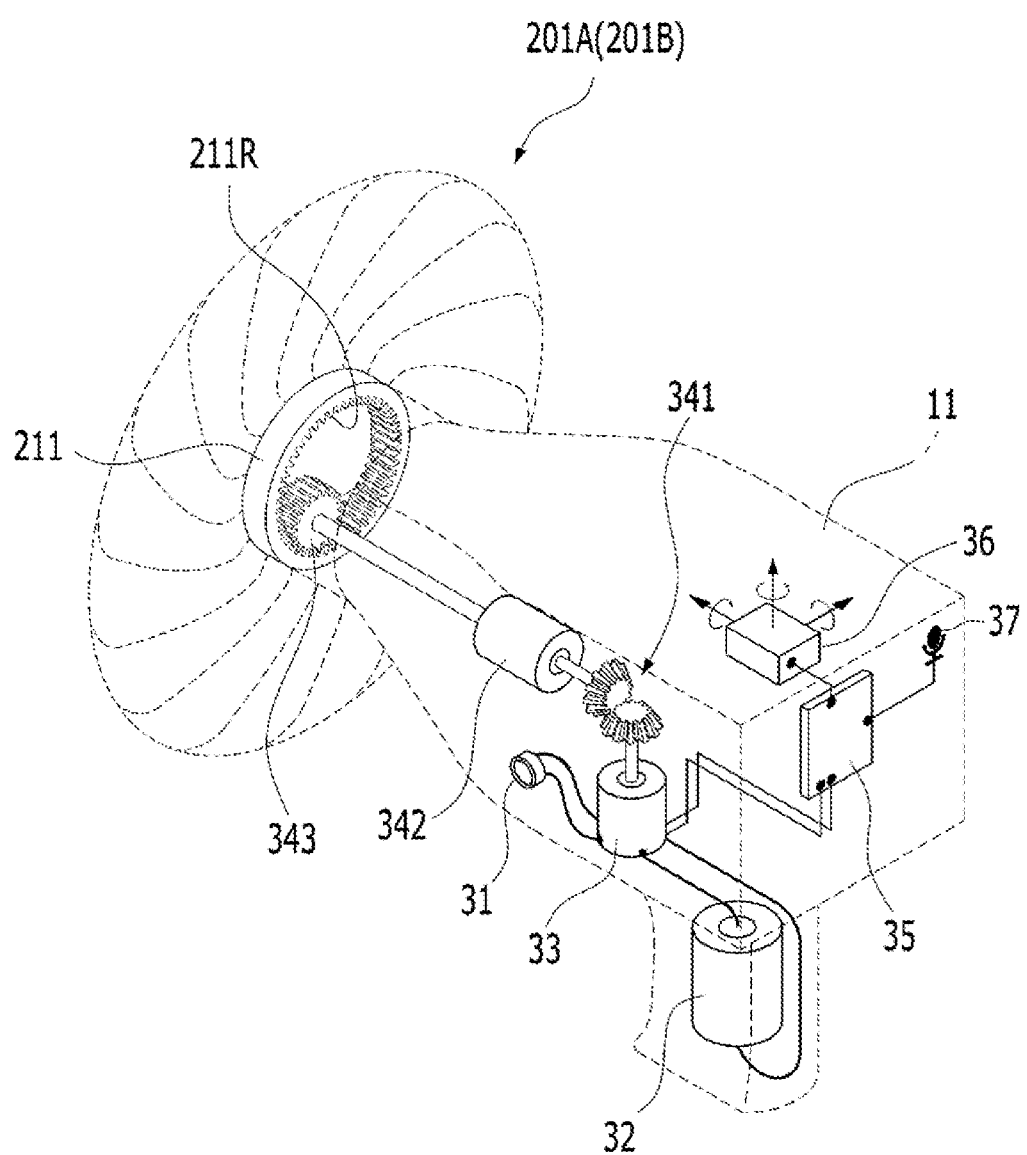
FIG. 10 is a diagram showing an example of a driving means for a rotary convertible backscattered ray shielding mechanism in an X-ray generator according to still another of the present invention.

FIG. 10 is a diagram showing an example of a driving means for a rotary convertible backscattered ray shielding mechanism in an X-ray generator according to an embodiment of the present invention.

In the above-described embodiments, the X-ray generator according to the present invention may be configured to automatically fold and unfold the rotary convertible backscattered ray shielding mechanisms 201A and 201B. Accordingly, the X-ray generator is provided with an electric motor 33 connected to a power supply unit 32 of the body 11 and a power transmission unit performing folding and unfolding operations of the convertible backscattered ray shielding mechanism by using the power of the electric motor 33. Meanwhile, for example, the power transmission unit may include a bevel gear 341, a speed reducer 342, and a pinion gear 343 provided on an output shaft of the speed reducer 342. The power transmission unit may be configured to rotate the first rotation ring 211 by engaging the pinion gear 343 with a gear 211R provided along a periphery of the first rotation ring 211. It is clear to those of ordinary skill in the art that power transmission mechanisms can be implemented in various forms.

The electric motor 33 and the power supply unit 32 are connected to a switch 31 that is exposed to outside the body 11 by a controller 35. Thus, the user can easily operate the convertible backscattered ray shielding mechanisms 201A and 201B according to the present invention with the switch 31.

Meanwhile, as described above, a foldable convertible backscattered ray shielding mechanism of the present invention performs folding and unfolding operations by using the electric motor 33 connected to the power supply unit 32 and the power transmission unit 341, 342, 343, and may be operated by various input means connected to the controller 35. For example, in addition to the input means having a function similar to an interface such as a switch, a motion recognition using a gyro sensor 36 or a speech recognition technique using a microphone 37 may be utilized in order to enhance the user convenience. A means such as the gyro sensor 36 and the microphone 37 may be provided in addition to the switch 31 or provided selectively.

In a case of a signal input using the switch 31, for example, the backscattered ray shielding mechanism may be set to perform folding and unfolding operations when inputs exceed a predetermined acceleration more than once. In a case of a signal input using the motion recognition, as a specific example, when a user moves the gyro sensor 36 located inside or outside the body by shaking within a predetermined time, the controller 35 recognizes the motion as an input and performs the folding or unfolding operation. Here, time may be set within 0 seconds to 3 seconds, preferably 2 seconds. In addition, the number of reciprocating movements may vary from 1 to 5 times, preferably 2 times.

In a case of a signal input using the microphone 37, the unfolding operation is performed by voice of word related to the unfolding operation such as, "open", "spread", "unfold", and so on in Korean, English, or other languages, and the folding operation is performed by voice of word related to the folding operation such as "close", "shut", "fold", and so on in Korean, English, or other languages. Here, input commands are not limited to those described above and may be variously set. In addition, a user may individually set an input command with specific words or numbers.

In addition, in order to maximize the user convenience, the operation of the backscattered ray shielding mechanism may be performed by synchronization with the X-ray generating switch. When the user pushes the X-ray generating switch, the unfolding operation of the backscattered ray shielding mechanism is performed at the same time, and when a set X-ray irradiation time passes, the signal input value to fold is automatically transmitted to perform the folding operation. Here, the X-ray irradiation time may be set based on the time the user inputs to the X-ray generating device.

The above-mentioned input means may be used alone or in combination with two or more means. A user may preliminarily select and set an input means which will be used.

Figure 11:
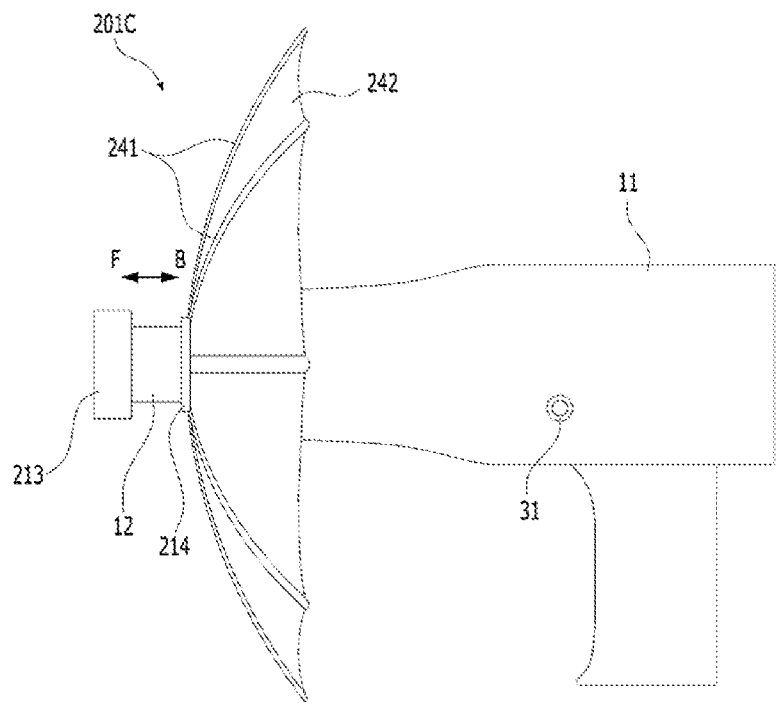
FIG. 11 is a diagram showing a foldable convertible backscattered ray shielding mechanism of an X-ray generating device according to still another embodiment of the present invention.

FIG. 11 is a diagram showing a foldable convertible backscattered ray shielding mechanism of an X-ray generating device according to an embodiment of the present invention.

According to the embodiment, the convertible backscattered ray shielding mechanism 201C may include a sliding ring 214 moving back and forth in an X-ray emission direction on a circumference of the X-ray emission port, multiple shielding strips 241 configured to move each other to be closed or apart each other in depending on a position of the sliding ring 214 and whose one ends are connected to the sliding ring 214, and a flexible shield 242 configured to be folded when the multiple shielding strips 241 are in close contact with each other and to be unfolded when the multiple shielding strips 241 flare.

As an example, a fixing ring 213 may be provided around the X-ray emission, which serves as a stopper when the sliding ring 214 moves toward an F direction along the X-ray emitting unit 12. Yet not shown in figures of the present invention, a mechanism structure in a form of a link may be provided between the flexible shield 242 and the body 11 of the figure to be connected to the body 11 and the shielding strips 241. The mechanism structure may be configured to unfold the multiple shielding strips 241 in the radial direction around the X-ray emission port and fold the multiple shielding strips 241 toward the body 11 according to a position of the sliding ring 214 in the same manner as a folding umbrella. Accordingly, in the embodiment, when the sliding ring 214 moves in the F direction, the shielding member, which is the multiple shielding strips 241 and the flexible shield 242, is folded and easy to store. On the contrary, when the sliding ring 214 moves in a B direction, the shielding member is unfolded and blocks the backscattered ray. Here as elsewhere the body 11 may be provided with the switch 31. In addition, the body 11 may be provided with a mechanism that automatically moves the sliding ring 214 at an inside thereof.

Figure 12:
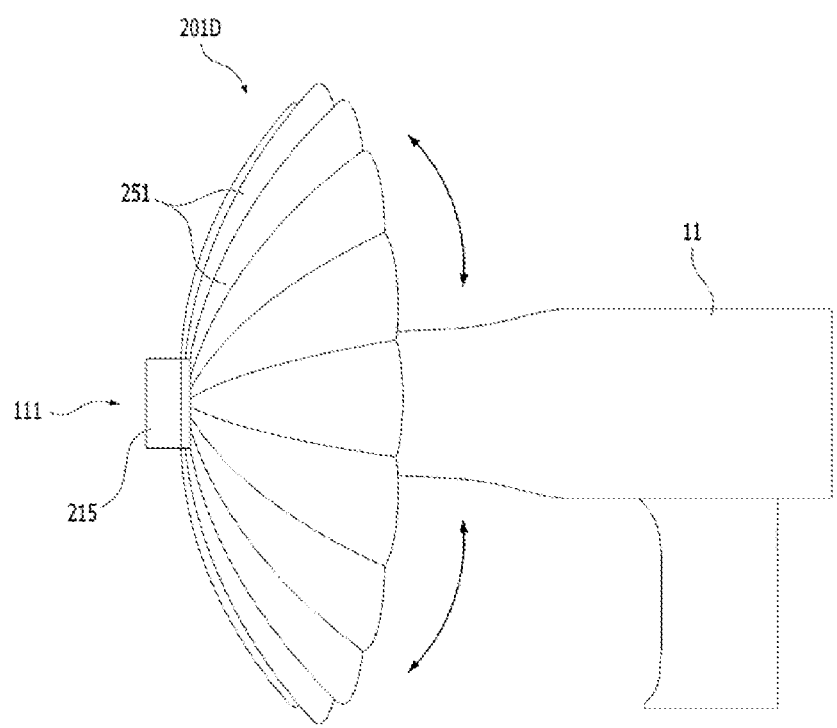
FIG. 12 is a diagram showing another foldable convertible backscattered ray shielding mechanism of an X-ray generating device according to still another embodiment of the present invention.

FIG. 12 is a diagram showing another foldable convertible backscattered ray shielding mechanism of an X-ray generating device according to an embodiment of the present invention.

According to the embodiment of the present invention, a convertible backscattered ray shielding mechanism 201D may be provided with multiple shielding blades 251 which are partially fixed as a form of hinge with respect to a fixing ring 215 fixing around the X-ray emission port 111. In this case, when the multiple shielding blades 251 are folded toward the body 11, more parts thereof overlap each other and the multiple shielding blades 251 are easy to be stored. On the other hand, when the multiple shielding blades 251 are unfolded in the radial direction around the X-ray emission port 111, it is possible to shield the user from the backscattered rays.

Accordingly, it should be understood that the present invention includes various modifications, additions and substitutions without departing from the scope and spirit of the invention as disclosed in the accompanying claims.

INDUSTRIAL APPLICABILITY

As described above, the present invention relates to the portable X-ray generating device and the backscattered ray shielding mechanism that is detachably or foldably provided thereon, which can be utilized in the fields of medical X-ray imaging devices including dental devices and non-destructive inspection devices in facilities, and the like.

The invention claimed is:

1. A backscattered ray shielding mechanism being mounted on a portable X-ray generating hand-held device to emit X-rays and blocking backscattered X-rays during X-ray emission, the backscattered ray shielding mechanism comprising:
  a shielding member detachably or foldably mounted as a convertible form on an X-ray emitting unit of the portable X-ray generating device and partially supported by the X-ray emitting unit,
  wherein the shielding member is fitted around the X-ray emitting unit and includes at least one support member partially connected thereto to support the shielding member, and
  wherein the at least one support member includes:
    at least one support ring being fitted around the X-ray emitting unit and
    at least one guide rail being attached to the support ring along a longitudinal direction of the X-ray emitting unit,
  wherein the shielding member is partially supported by the guide rail and moves along the guide rail.

2. The mechanism of claim 1, wherein the shielding member is a lead free lightweight shielding sheet.

3. The mechanism of claim 2, wherein the shielding member is provided as a curtain shape and suspended from the support member.

4. The mechanism of claim 3, wherein the shielding member is woven tungsten filaments.

5. The mechanism of claim 1, wherein the X-ray emitting unit is cylindrical and the at least one support member is a ring for rotating around the X-ray emitting unit or moving along a longitudinal direction of the X-ray emitting unit.

6. The mechanism of claim 1, wherein the shielding member includes an X-ray shielding material, which is lead-free and has a specific gravity smaller than that of lead.

7. The mechanism of claim 6, wherein the X-ray shielding material is selected from a group consisting of tungsten, barium, bismuth, and mixtures thereof.

8. A backscattered ray shielding mechanism being mounted on a portable X-ray generating hand-held device to emit X-rays and blocking backscattered X-rays during X-ray emission, the backscattered ray shielding mechanism, comprising:
  a shielding member detachably or foldably mounted as a convertible form on an X-ray emitting unit of the portable X-ray generating device and partially supported by the X-ray emitting unit,
  wherein the shielding member is fitted around the X-ray emitting unit and includes at least one support member partially connected thereto to support the shielding member, and
  wherein the at least one support member includes:
    at least one support ring being fitted around the X-ray emitting unit; and
    at least one connection bar being attached to the support ring along a longitudinal direction of the X-ray emitting unit and having first and second connection bars disposed along the longitudinal direction, and
  wherein the first and second connection bards side along with each other to overlap some parts thereof or are hinged to be bent such that each length thereof is adjusted and the shielding
  sheet moves according to the adjust length thereof.

9. A portable X-ray generating device comprising:
a body being provided with an X-ray generator;
an X-ray emission port being disposed in front of the body from which X-rays are emitted; and
a convertible backscattered ray shielding mechanism being mounted around the X-ray emission port of the body in a foldable form, and blocking backscattered rays in use and being folded to be stored when unused,
wherein the convertible backscattered ray shielding mechanism includes:
a rotation ring rotating around the X-ray emission port; and
multiple shielding blades being folded and unfolded with association with a rotation of the rotation ring.

10. The device of claim 9, wherein the convertible backscattered ray shielding mechanism includes:
a rotation ring rotating around the X-ray emission port;
multiple shielding strips configured to move each other to be closed or apart each other in association with a rotation of the rotation ring; and
a flexible shield connecting between the multiple shielding strips, and being configured to be folded when the multiple shielding strips are in close contact with each other and to be unfolded when the multiple shielding strips flare.

11. The device of claim 9, wherein the convertible backscattered ray shielding mechanism includes:
a sliding ring moving back and forth in an X-ray emission direction on a circumference of the X-ray emission port;
multiple shielding strips configured to move each other to be closed or apart each other in depending on a position of the sliding ring and whose one ends are connected to the sliding ring; and
a flexible shield being configured to be folded when the multiple shielding strips are in close contact with each other and to be unfolded when the multiple shielding strips flare.

12. The device of claim 9, further comprising:
an electric motor being connected to a power supply unit of the body;
a power transmission unit performing folding and unfolding operations of the convertible backscattered ray shielding mechanism by using power of the electric motor; and
a controller controlling the operation of the power transmission unit according to an input of a user.

* * * * *